United States Patent [19]

Walman

[11] Patent Number: 5,078,740
[45] Date of Patent: Jan. 7, 1992

[54] INTRAOCULAR LENS

[76] Inventor: Gerald B. Walman, 5535 N. 4th St., Phoenix, Ariz. 85012

[21] Appl. No.: 503,328

[22] Filed: Apr. 2, 1990

[51] Int. Cl.⁵ ............................................. A61F 2/16
[52] U.S. Cl. ..................................................... 623/36
[58] Field of Search ............................................ 623/6

[56] References Cited

U.S. PATENT DOCUMENTS

| | | | |
|---|---|---|---|
| Re. 33,039 | 8/1989 | Arnott | 623/6 |
| 4,280,232 | 7/1981 | Hummel | 623/6 |
| 4,402,579 | 9/1983 | Poler | 351/160 R |
| 4,409,691 | 10/1983 | Levy | 623/6 |
| 4,423,809 | 1/1984 | Mazzocco | 206/5.1 |
| 4,424,597 | 1/1984 | Schlegel | 623/6 |
| 4,435,050 | 3/1984 | Poler | 351/160 R |
| 4,439,873 | 4/1984 | Poler | 623/6 |
| 4,450,593 | 5/1984 | Poler | 623/6 |
| 4,476,591 | 10/1984 | Arnott | 623/6 |
| 4,494,254 | 1/1985 | Lopez | 623/6 |
| 4,540,417 | 9/1985 | Poler | 604/895 |
| 4,573,998 | 3/1986 | Mazzocco | 623/6 |
| 4,575,373 | 3/1986 | Johnson | 623/6 |
| 4,629,460 | 12/1986 | Dyer | 623/6 |
| 4,666,444 | 5/1987 | Pannu | 623/6 |
| 4,704,122 | 11/1987 | Portnoy | 623/6 |
| 4,710,195 | 12/1987 | Giovinazzo | 623/6 |
| 4,711,638 | 12/1987 | Lindstrom | 623/6 |
| 4,720,286 | 1/1988 | Bailey et al. | 623/6 |
| 4,734,095 | 3/1988 | Siepser | 623/6 |
| 4,778,463 | 10/1988 | Hetland | 623/6 |
| 4,795,460 | 1/1989 | Anis | 623/6 |
| 4,804,361 | 2/1989 | Anis | 623/6 |
| 4,842,600 | 6/1989 | Feaster | 623/6 |
| 4,842,602 | 1/1989 | Nguyen | 623/6 |
| 4,863,463 | 9/1989 | Tjan | 623/6 |
| 4,863,465 | 9/1989 | Kelman | 623/6 |
| 4,871,362 | 10/1989 | Nurmamedov et al. | 623/6 |
| 4,872,876 | 10/1989 | Smith | 623/6 |
| 4,878,911 | 11/1989 | Anis | 623/6 |
| 4,880,427 | 11/1989 | Anis | 623/6 |
| 4,888,012 | 12/1989 | Horn et al. | 623/6 |
| 4,888,014 | 12/1989 | Nguyen | 623/6 |
| 4,902,293 | 2/1990 | Feaster | 623/6 |
| 4,932,967 | 6/1990 | Kansas | 623/6 |

Primary Examiner—Ronald Frinks
Attorney, Agent, or Firm—Cahill, Sutton & Thomas

[57] ABSTRACT

The intraocular lens implant embodies laterally extending dual segmented haptics which define a circular flexible fixation member upon implantation within the capsular bag to tauten the posterior wall and inhibit opacification.

21 Claims, 3 Drawing Sheets

INTRAOCULAR LENS

BACKGROUND OF THE INVENTION

1. Field of the Invention

The present invention relates to intraocular lenses and, more particularly, to lenses having stable bendable haptics defining a circular flexible fixation member when implanted.

2. Description of the Prior Art

The visual rehabilitation of a patient afflicted with cataract has been a controversial topic within the cognoscente for decades. To understand the concept of intraocular lens implants, one must first have an intimate knowledge of the anatomy of the eye and the characteristics of a cataract. Light enters through the cornea of an eye. The cornea is a clear transparent tissue that serves as a window which allows entry of light and provides some amount of focusing capability. The light traverses the anterior chamber and penetrates the crystalline lens. The lens acts as a major focusing element for the light. The light, after being focused by the lens, continues on its path through the vitreous and impinges upon the retina. The impinging light is transformed into electrical impulses by the reaction of layers of complex specialized retinal nerves. The nerves transmit the electrical impulses to the brain which translates them into visual sensations.

The word cataract refers to a clouding of the normally clear lens. The causes of cataract need not be reviewed except to say that senile cataract is an extremely common affliction of patients over the age of sixty and leads to varying amounts of significant visual disability. When a cataract is present, the light normally penetrating the crystalline lens for focusing is impaired by the clouded areas. When the cataract becomes severe enough, the only treatment available is surgical removal of the cataract which is equivalent to surgical removal of the crystalline lens. At the present time, there are no medicinal cures for most patients afflicted with cataract.

With the surgical removal of the crystalline lens, the resulting eye is deficient in focusing power. In the early years of cataract surgery, this deficiency of focusing power was corrected by using a thick lens held in front of the eye by a spectacle frame. Improvements in visual rehabilitation came with the availability of contact lenses. A contact lens is located on the surface of the cornea and compensates for the deficiency in focusing power.

A third alternative of visual rehabilitation is the use of an intraocular lens implant (IOL). An IOL is a small plastic lens with lens support structures that is inserted into the eye by surgery. The difficulties enumerated above attendant thick lenses and contact lenses are completely eliminated. Moreover, the patient has no sensation of the presence of the IOL and if the implant is successful, the IOL may be in the eye permanently to replace the lost focusing power of the removed crystalline lens. A preferred plastic is polymethyl methacrylate (PMMA) as techniques are now known for molding or otherwise fabricating an IOL from this material.

An intraocular lens falls into one of three broad categories depending upon its position within the eye. An anterior chamber intraocular lens is placed within the anterior chamber in front of the iris. Its fixation is dependent on various styles of loops that are supported in the angles of the anterior chamber, whereby the iris tissue is allowed to move freely. From a technical standpoint, the anterior chamber IOLs are the easiest to implant. The difficulties with prior art anterior chamber IOLs include: (1) deficient manufacturing methods which leave rough edges on the implant and result in chronic irritation (iritis), elevated intraocular pressure (glaucoma) and bleeding from within the anterior chamber (hyphema); (2) the lens support structure is of solid plastic construction, rather than flexible loop construction, which can lead to blockage of the normal aqueous flow within the eye (pupillary block glaucoma); (3) the lack of sufficient flexibility of the support structure leads to difficulties with tenderness on touching of the eye and normal movements during one's daily activities can lead to chronic irritation within the eye; (4) the prior art anterior chamber IOLs have to be matched in size to the patient's eye which increases IOL inventory problems. More importantly, without accurate measurements of the patient's eyes, an inflexible or insufficiently flexible IOL that is too small results in increased movement of the implant that can lead to chronic irritation while an implant that is too large tends to distort the eye, cause discomfort and lead to chronic irritation. The major advantage of an anterior chamber IOL is that it may be used after either intracapsular or extracapsular surgery.

An iris supported IOL is an implant that depends on iris tissue or a combination of iris tissue and capsular tissue for its support. It has significant disadvantages because of its lack of uniplanar design and its constant iris contact.

A posterior chamber IOL is inserted behind the iris to position the lens in the exact anatomical position of the previously removed cataract or crystalline lens. The major disadvantage of prior art posterior chamber IOLs is that the cataract must be removed by extracapsular techniques. The advantages attendant posterior chamber IOLs in general include: (1) fixation at the posterior capsule provides good stability to the eye; (2) as no iris fixation is present, the pupil behaves normally; (3) the implant is uniplanar and therefore is generally easy to insert without damaging other structures; (4) dislocation is rare but if it should occur, the implant does not dislocate anteriorly to damage the cornea; and (5) the patient is visually rehabilitated as nearly as is physiologically possible since the implant is in the exact location as the previously removed crystalline lens.

SUMMARY OF THE INVENTION

The intraocular lens implant is a posterior IOL implantable within the capsular bag and incorporates a lens having a pair of haptics extending from essentially diametrically opposed locations at the perimeter of the lens. Each haptic includes a first and second segment. The first segment extends from the perimeter of the lens generally tangentially and non radially with a constant curvature or a reducing curvature. The second segment is joined to the first segment at its extremity and may extend with a constant curvature or a varying curvature doubled back upon the first segment. The extremity of the second segment of each haptic extends past the junction between the first and second segments of the other haptic in an overlapping relationship therewith. Preferably, the distal end or extremity of the second segment of each haptic is disposed radially outwardly of the overlapped part of the other haptic prior to implantation. Upon implantation, the extremity of the second segment of each haptic is bent inwardly toward the lens to overlap and overlie the proximal or interior end of the second segment of the other haptic whereby both second segments define a generally circular fixation surface for supporting the lens within the capsular bag. Any compressive forces exerted upon the haptics after implantation will result in bending of either or both segments of either or both haptics. Such bending may induce rotation of the lens about its optical axis but will not urge bowing of the implant or other translation of the lens along its optical axis.

It is therefore a primary object of the present invention to provide haptics for an intraocular lens having a pair of haptics which define a circular flexible fixation member when implanted.

Another object of the present invention is to provide an IOL with a pair of haptics having dual segments folded back upon one another to define a circular fixation member upon implantation.

Still another object of the present invention is to provide an IOL with a pair of haptics wherein the terminal end of each haptic overlaps and is disposed radially outwardly of the other haptic prior to implantation.

Yet another object of the present invention is to provide each haptic of a pair of haptics for fixating an IOL within the capsular bag wherein each haptic includes a first curved segment terminating at a junction and a second curved segment extending from the junction back upon and radially outwardly of the first segment to a terminal end overlapping the second segment of the other haptic.

A further object of the present invention is to provide an intraocular lens implant which may be used in any sized eye within a large range of eye sizes.

A yet further object of the present invention is to provide an intraocular lens implant which accommodates and relieves imposed compressive forces by causing rotation of the lens about its optical axis and without bowing.

A yet further object of the present invention is to provide an IOL for the posterior chamber which allows reliable centration and symmetrical stretch of the capsular bag upon implantation.

A still further object of the present invention is to provide an IOL having a pair of haptics which extend for 360°. within the capsular bag upon implementation.

A still further object of the present invention is to provide an IOL having a pair of haptics for maintaining the posterior wall of the capsular bag uniformly taut.

A still further object of the present invention is to provide an IOL having a lens maintained by its haptics in direct and continuing contact with the posterior wall of the capsular bag.

A still further object of the present invention is to provide an IOL having haptics defining an initial diameter of approximately 12.5 mm. which can be compressed to approximately 6.0 mm. during insertion for fixation within the capsular bag.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which.

DESCRIPTION OF THE PREFERRED EMBODIMENT

Cataract extractions are currently predominantly done in extracapsular fashion. With this technique, the posterior capsule is left intact. Posterior capsular opacification, or clouding, may occur in 10% to 35% of the cases. Present management of this problem involves primarily the use of a YAG laser to form a capsulotomy.

Methods for inhibiting posterior capsular clouding include the belief that direct contact of an implant with the posterior capsule inhibits capsular opacification. Accordingly, implants have been manufactured with a convex posterior side in an attempt to inhibit this opacification. Other implants have been manufactured with a laser ring for the purpose of contact inhibition of this clouding. Despite the multitude of designs of implants to inhibit such capsular opacification, it is well known that the incidence of posterior capsular clouding continues to be high.

A current theory among some ophthalmologists involves the theory that folding and contraction of the posterior capsule leads to actual opacification. It is believed that a capsule that is stretched with no folding tends not to show opacification. On the basis of this theory, intraocular lens implants have been devised that have stretched the capsule. Many of these implants, however, do not have 360° contact of the distal portion to stretch the capsule and the capsule therefore has areas where folding can lead to tunnels of cells growing inwardly. Attempts have been made to devise a disk lens which essentially stretches the capsule throughout 360°. A difficulty with such a lens is that the lens itself is too bulky to easily insert it into the eye and within the capsule.

Figure 1:
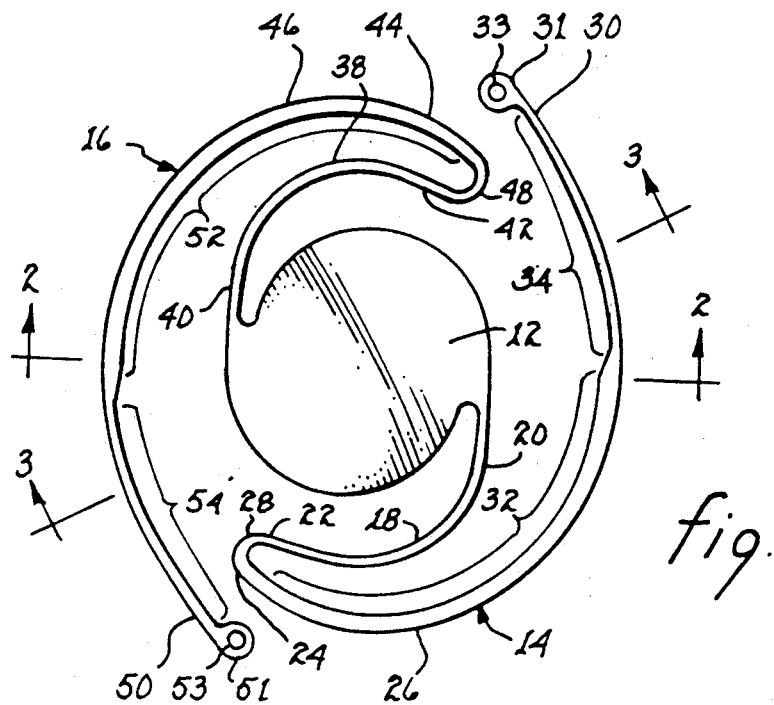
FIG. 1 illustrates a plan view of an intraocular lens prior to implantation.
Figure 2:
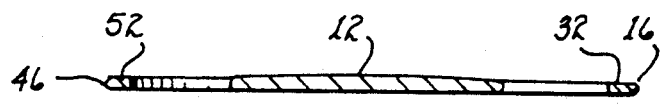
FIG. 2 is a cross sectional view taken along lines 2—2, as shown in FIG. 1.
Figure 3:
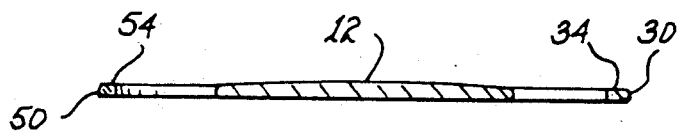
FIG. 3 is a cross sectional view taken along lines 3—3, as shown in FIG. 1.

Referring jointly to FIGS. 1, 2 and 3, there is illustrated a configuration of an intraocular lens (IOL) 10 which will achieve the goal of stretching the capsule throughout 360° in a very simple manner. Referring to FIG. 1, IOL 10 includes a lens 12 sized and of a power compatible with the optical requirements of &he patient in whose eye it is to be implanted. Nominally, the lens is 6.0 mm. in diameter. Haptics 14 and 16 extend from generally diametrically opposed locations at the perimeter of lens 12. Haptic 14 includes a first segment 18, which segment may extend generally tangentially from the perimeter of the lens. The curvature of the first segment may be generally constant throughout its major length or the rate of curvature may increase, decrease or vary. Inner end 20 extending from lens 12 may include a non curved section. Outer end 22 of first segment 18 joins with inner end 24 of second segment 26 of haptic 14. Junction 28, formed by the joining of outer end 22 and inner end 24, may be semicircular as depicted or of other configuration compatible with manufacturing requirements, the procedure to be performed and requirements of flexibility/resiliency.

Second segment 26 of haptic 14 is folded back upon first segment 18 by junction 28. The second segment varies in cross sectional area from proximal or inner end 24 to outer end 30; for ease of manufacturing, such change in cross section may be readily accomplished by maintaining a uniform thickness of the segment but incorporating a reduced width for a part of the second segment. Specifically, section 32 is of a first width, nominally 0.15 mm., and section 34 is of a second width, nominally 0.11 mm. The thickness of both sections may be constant at 0.15 mm.

To provide an essentially circular ring like configuration presented by haptics 14 and 16 upon implantation, section 32 may be of constant curvature to define a segment of a circle. Alternatively, section 34 may be configured to have a progressively reducing curvature throughout its length or from the junction between the two sections to distal or outer end 30. This reduced curvature configuration of section 34 of second segment 26 serves two purposes. First, during manufacture of the IOL, a one piece IOL can be made of PMMA or other material if there is no overlap of components; this criteria is satisfied by the IOL shown in FIG. 1. Second, after implantation, section 34 of second segment 26 will be urged to conform with the generally circular inner perimeter of the capsular bag. The resulting conformance will tend to bend section 34 to a generally constant curvature section much like a curved extension of section 32. This imposed bending of section 34, alone or in combination with a slight compression of section 32, will securely but resiliently and flexibly secure the IOL within the capsular bag.

Haptic 16 includes components identical with corresponding ones of haptic 14, such as first segment 38, inner end 40, outer end 42, inner end 44, second segment 46, junction 48, outer end 50, section 52 and section 54.

Upon implantation of IOL 10, the distal or outer ends of the second segments of haptics 14 and 16 will be bent inwardly to individually define with their corresponding proximal or inner ends (26,46), respective more than semi circular fixation means. Terminal ends 31,51 will be in overlapping relationship with the corresponding inner ends 44 and 24, respectively, of the other haptic. As illustrated, terminal ends 31,51 may include apertures 33,53 for receiving surgical instruments and to assist in manipulation of the IOL during implantation and removal. With or without the apertures terminal ends are bulbous like to minimize the likelihood of penetration or injury therefrom to the tissue of the capsular bag.

Figure 4:
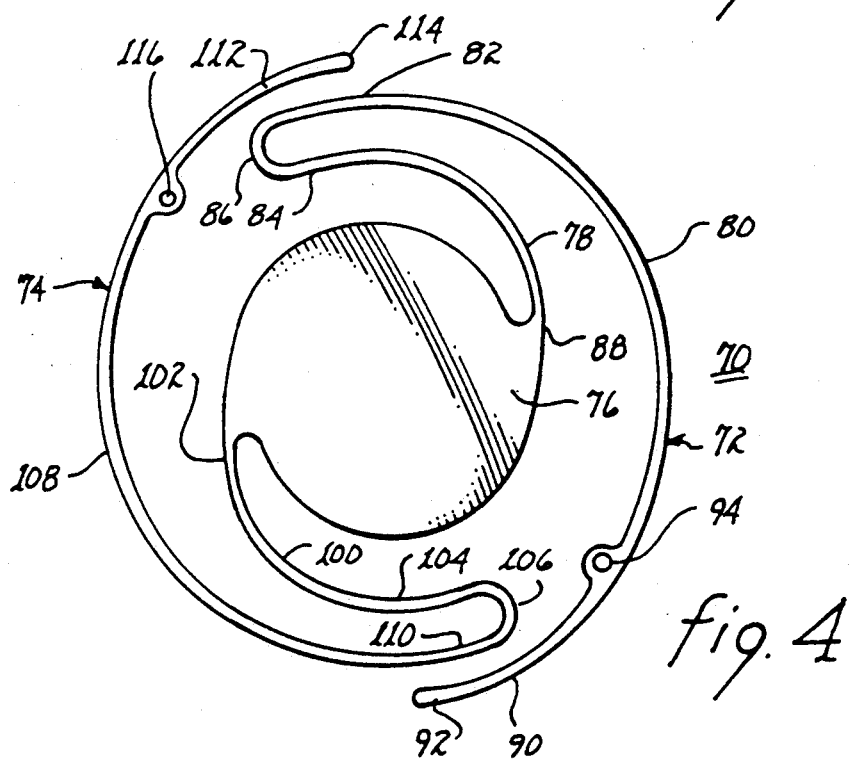
FIG. 4 is a plan view of a first variant of an intraocular lens prior to implantation.
Figure 5:
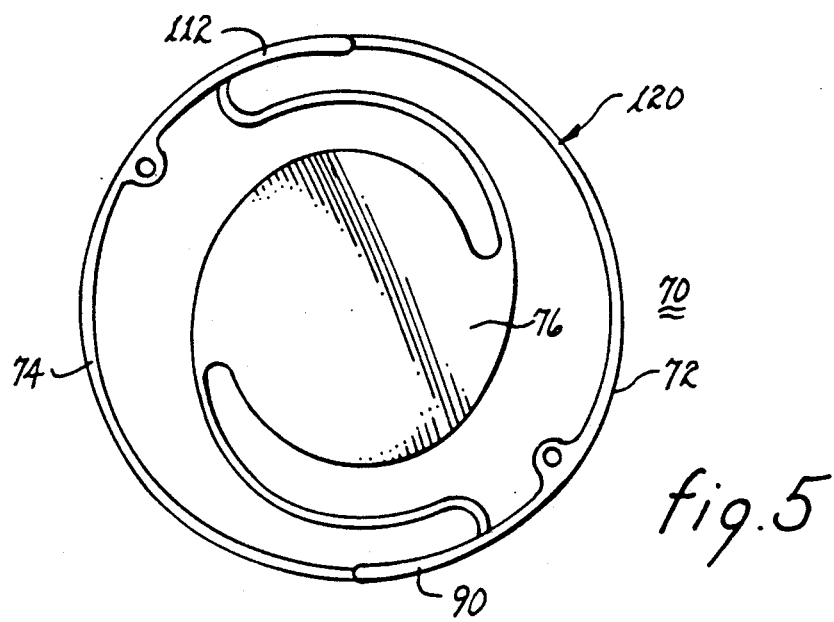
FIG. 5 is a plan view illustrating the configuration of the first variant intraocular lens upon implantation.

Referring jointly to FIGS. 4 and 5, there is illustrated a first variant 70 of an IOL. A pair of haptics 72,74 support a lens 76. Haptic 72 includes a first segment 78 extending from the perimeter of lens 76. A second segment 80 includes a proximal or an inner end 82 joined with outer end 84 of first segment 78 to form a junction 86 therebetween. Inner end 88 of first segment 76 may be curved or may include a straight section. Distal or outer end 90 includes a teardrop shaped or expanded terminal end 92 to reduce the probability of penetrable engagement with or injury to the capsular bag during implantation. An aperture 94 may be disposed along second segment 80 for receiving a surgical instrument and to aid manipulation of the IOL during an implantation procedure. Preferably, the material defining aperture 94 is inwardly of the outer boundary of second segment 80 to maintain a smooth curved supporting surface adjacent the capsular bag.

Haptic 74 includes components paralleling those of haptic 72. In particular, it includes first segment 100 having inner end 102 and outer end 104 terminating at junction 106. A second segment 108 includes a proximal or an inner end 110 extending from junction 106 in folded back orientation with respect to first segment 100. Distal or outer end 112 of second segment 108 includes a terminal end 114. Aperture 116 may be formed along the second segment to assist in manipulation of the variant during implantation and removal.

First segments 78 and 100 of haptics 72,74, respectively, may be of constant curvature or of varying curvature. Junctions 106 may be essentially semicircular in planform as illustrated or the outer end of the first segment may define with the inner end of the second segment an acute angle. Other configurations for the junctions may also be embraced. As particularly shown in planform in FIG. 4, second segments 80,108 of haptics 72,74, respectively, do not define in their relaxed state (FIG. 4) sections of a circle common to both. The distal or terminal end of each second segment is laterally or radially outwardly of an overlapped part of the proximal or inner end of the other second segment. The second segments may be of a constant curvature, may have a reduced degree of curvature extending from the respective junction to the respective terminal end or the curvature may increase from the respective junction to the respective terminal end.

Upon implantation, second segments 80,108 of haptics 72,74 will be placed within the interior perimeter of the capsular bag. Since the overall circular size of IOL variant 70 conforms with the circular size of the capsular bag, outer segments 90 and 112 of haptics 72,74, respectively, will overly and overlap the inner end of the other respective second segment, as particularly illustrated in FIG. 5. The resulting planform of IOL variant 70 represents an essentially circular fixation member, designated by numeral 120, circumscribing and having centrally disposed therewithin lens 76. To ensure overlying of the overlapping respective outer ends 90,112 with respect to inner ends 110,82, respectively, the outer ends may be prebent out of the plane defined by the remaining part of the respective haptic. This configuration is illustrated in the cross sectional view depicted in FIG. 7.

Figure 6:
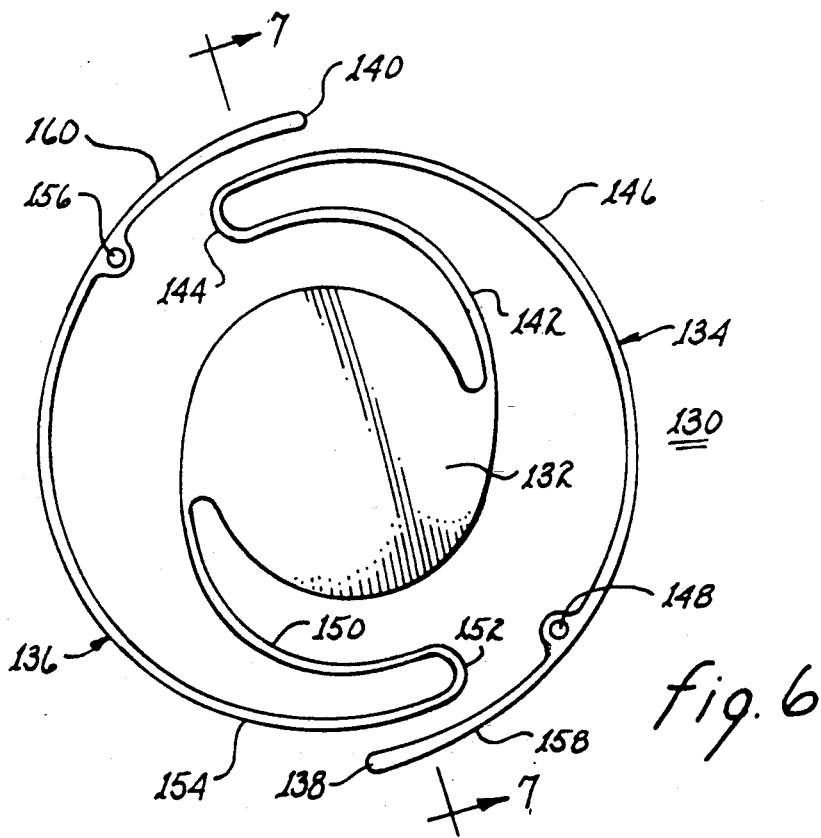
FIG. 6 is a plan view illustrating a second variant of an intraocular lens prior to implantation.
Figure 7:
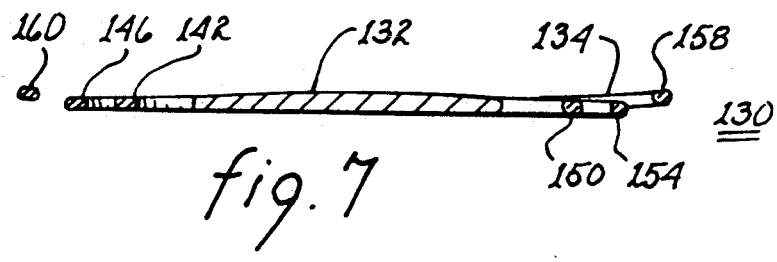
FIG. 7 is a cross sectional view taken along lines 7—7, as shown in FIG. 6.
Figure 8:
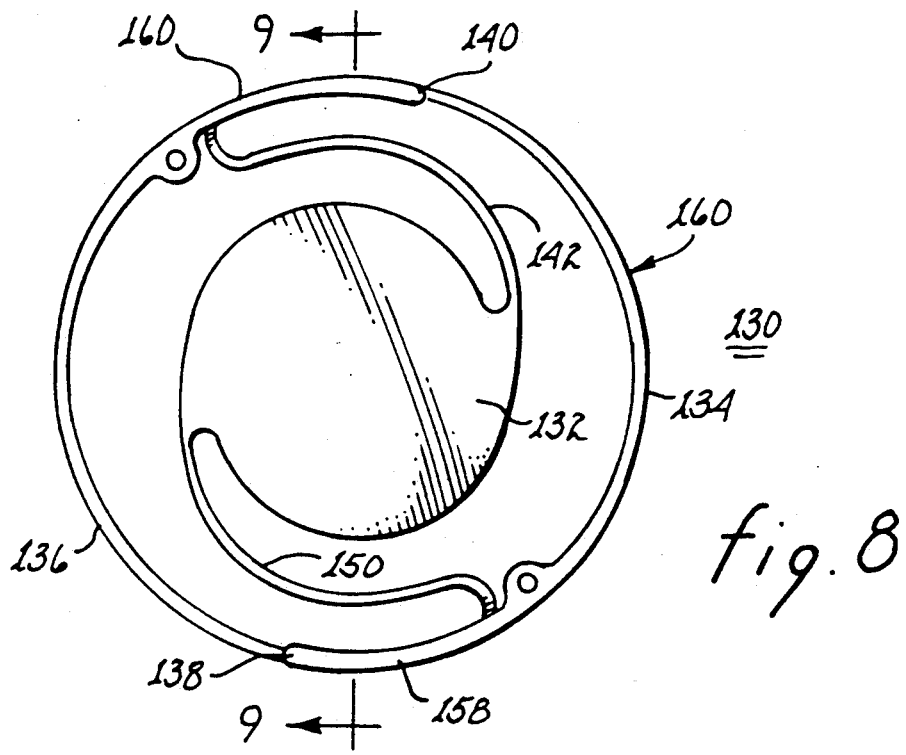
FIG. 8 is a plan view of the second variant intraocular lens after implantation.

Referring jointly to FIGS. 6, 7 and 8, there is shown a second IOL variant 130. This variant includes a lens 132 having a pair of haptics 134,136 extending therefrom. Distal or terminal ends 138,140 are bulbous or teardrop shaped to reduce the likelihood of inadvertent penetration of or damage to the capsule bag during implantation or removal of the IOL. Additionally, the blunted ends will tend to be less irritating to the tissues in contact therewith during normal rubbing of the eye and other expected activities of a patient. First segment 142 of haptic 134 extends from the perimeter of lens 132 to a junction 144 with second segment 146 of the haptic. The second segment is folded back upon the first segment. An aperture 148 may be formed in second segment 146 to receive a surgical instrument and permit ease of manipulation of the IOL during the implanting procedure.

Haptic 136 is essentially a mirror image of haptic 134. It also includes a first segment 150, a junction 152 for joining first segment 150 with a second segment 154. An aperture 156 may be formed within the second segment to receive a surgical instrument and facilitate manipulation of the IOL during the implanting procedure. The curvatures of first segments 142,150 may be constant, may be increasing or may be decreasing. Moreover, a section of each of the first segments proximate lens 132 may be straight.

The curvatures of second segments 146 may be essentially constant from a point between the respective junctions and the respective distal ends to the respective distal ends; for example, the curvature may be constant from the manipulation aperture to the distal end. Uniform resistance against bending or unbending of the second segments will be enhanced by maintaining the width and thickness of a substantial distal section of the second segments uniform. Inwardly from a point, such as the respective manipulation aperture in the second segments to a location at or short of the junctions ends of the respective second segments, the second segments are thinned. Such thinning may most easily be accomplished by reducing the width either abruptly or in tapered manner. The curvature of the essentially constant curvature distal sections of second segments 146,154 is commensurate with the general circle defined by the capsular bag into which the IOL is to be implanted. The curvature of thinned proximal sections of second segments 146,154, respectively, is reduced from that of the contiguous part of the respective second segment to place the respective terminal ends radially outwardly from the respective junctions and to provide overlap by the terminal end of one second segment with the other second segment, as illustrated in FIGS. 6 and 7.

Upon implanting second variant 130 within the capsular bag, terminal ends 138,140 of haptics 134,136 will be forced inwardly by the confine represented by the capsular bag. This inward movement is accommodated by bending of the thinned portion provided by the proximal sections. The resulting movement of the haptics will also tend to draw the haptics circularly toward one another until the second segments of the two haptics define a circular fixation member 160, as depicted in FIG. 8. It is to be understood that the second segments need not have formed therein manipulation apertures 148,156. Instead, these apertures, and the structure forming the apertures can be eliminated without departing from the heart of the invention.

Figure 9:
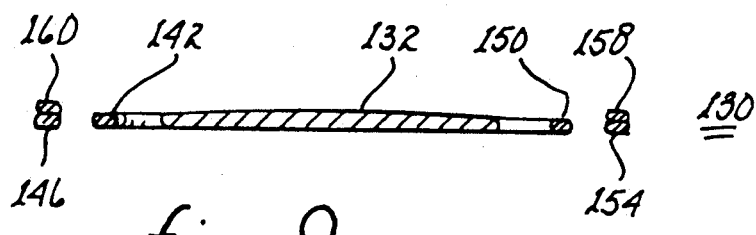
FIG. 9 is a cross sectional view taken along lines 9—9, as shown in FIG. 8.

To ensure coincident overlap of the outer ends of each second segment with the other second segment, the outer ends may be bent somewhat upwardly to an extent essentially equivalent to the thickness of the haptic it will overly, as depicted in FIG. 7. Upon implantation, outer ends 158,160 will be drawn radially inwardly into overlying and overlapping relationship with haptics 154,146, respectively, as particularly illustrated in FIG. 9.

Figure 10:
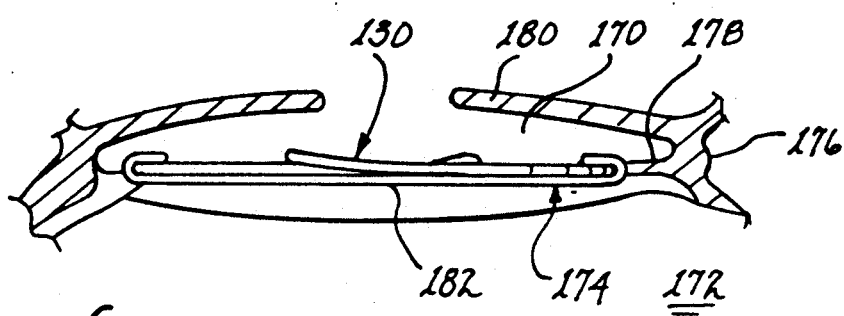
FIG. 10 illustrates a cross sectional view of the intraocular lens disposed within a capsular bag.

FIG. 10 illustrates an implanted intraocular lens, such as second variant 130. After extra capsular cataract extraction, posterior chamber 170 of an eye 172 includes a capsular bag 174 attached to ciliary body 176 by zonular fibers 178. Iris 180 is disposed anteriorly of the capsular bag. Upon implantation of IOL 10, first variant 70 or second variant 130 within the capsular bag, the slightly compressed haptics will urge flattening and stretching of posterior wall 182 of the capsular bag. Because the outwardly oriented forces exerted by the haptics is generally uniformly applied throughout 360°, sufficient concentration of forces by the fixation member to irritate the tissues anywhere along the contact point is precluded. Despite the low fixation force urged by any incremental segment of either of the two haptics, the totality of fixation forces exerted by both haptics will retain the lens positionally fixed.

The stretching of the posterior wall will prevent folding of tissue of the capsular bag and one potential cause for opacification will be eliminated. The stretched posterior wall will, due to it being stretched, lie adjacent and in contact with the posterior lens surface to enhance delay or elimination of opacification of the posterior wall.

In the event of disturbance to the eye, such as by rubbing, jarring one's head and similar normal activities, any compressive forces exerted upon the haptics will, due to the folded back configuration of the first and second segments of each haptic, urge rotation of the lens about its optical axis instead of bowing of the IOL. It is to be understood that the resistance to bending of each haptic is a function of the material of the haptic as well as its cross sectional area and the relationship between the width and thickness of each segment of each haptic.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. An intraocular lens for implantation in a human eye and defining a circular fixation member disposed within the capsular bag on implantation, said intraocular lens comprising in combination:
    a) a lens for focusing light entering the eye, said lens having an optical axis and a plane normal to the optical axis;
    b) a flexible first haptic extending from said lens, said first haptic including a first segment having an inner end and an outer end, a second segment having an inner end and an outer end and a first junction joining the outer end of said first segment with the inner end of said second segment and folding said second segment back over said first segment, said second segment including a first section and a second section and wherein said second section is less flexible then said first section for encouraging said first section to flex in conformance with forces imposed by the capsular bag;
    c) a flexible second haptic extending from said lens, said second haptic including a first segment having an inner end and an outer end, a second segment having an inner end and an outer end, and a second junction joining the outer end of said first segment and the inner end of said second segment and folding said second segment back over said first segment, said second segment including a first section and a second section and wherein said second section is less flexible than said first section for encouraging said first section to flex in conformance with forces imposed by the capsular bag;

d) said second segment of said first haptic including a terminal end overlapping said second junction in response to flexing of said first section of said second segment; and e) said second segment of said second haptic including a terminal end overlapping said first junction in response to flexing of said first section of said second segment.

2. The apparatus as set forth in claim 1 wherein each of said first segment and said second segment of said first haptic and said first segment and said second segment of said second haptic is curved.

3. The apparatus as set forth in claim 1 wherein prior to implantation of said intraocular lens said terminal end of said first haptic is disposed laterally outwardly of said second junction and said terminal end of said second haptic is disposed laterally outwardly of said first junction.

4. The apparatus as set forth in claim 3 wherein each of said second segment of said first haptic and said second segment of said second haptic is curved.

5. The apparatus as set forth in claim 4 wherein said terminal end of said first haptic overlapping said second junction is displaced from the plane normal to the optical axis with the remaining part of said first haptic being in the plane normal to the optical axis of the overlapping the overlapped inner end of said second segment of said second haptic on implantation of said intraocular lens in response to flexing of said first section of said second segment and wherein said terminal end of said second haptic overlapping said first junction is displaced from the plane normal to the optical axis with the remaining part of said second haptic being in the plane normal to the optical axis for overlapping the overlapped inner end of said second segment of said first haptic on implantation of said intraocular lens in response to flexing of said first section of said second segment.

6. The apparatus as set forth in claim 5 wherein said first section of said second segment of said first haptic and said first section of said second segment of said second haptic are of reduced cross sectional area to be more responsive to bending than the respective second section of each of said second segments.

7. The apparatus as set forth in claim 6 wherein said first sections of each of said second segments are disposed distally of the respective one of said second segments.

8. The apparatus as set forth in claim 7 wherein each of said terminal ends of said first and second haptics is tear drop shaped to reduce the possibility of abrading and traumatizing the capsular bag.

9. The apparatus as set forth in claim 6 wherein said first sections of each of said second segments are disposed proximally of the respective one of said second segments.

10. The apparatus as set forth in claim 9 wherein each of said terminal ends of said first and second haptics is tear drop shaped to reduce the possibility of abrading and traumatizing the capsular bag.

11. The apparatus as set forth in claim 1 wherein said first section of said second segment of said first haptic and said first section of said second segment of said second haptic are of reduced cross sectional area to be more responsive to bending than the respective second section to each of said second segments.

12. The apparatus as set forth in claim 11 wherein said first sections of each of said second segments are disposed distally of the respective one of said second segments.

13. The apparatus as set forth in claim 11 wherein said first sections of each of said second segments are disposed proximally of the respective one of said second segments.

14. An intraocular lens for implantation within the capsular bag of a human eye, said intraocular lens comprising in combination:

a) a lens for focusing light entering the eye;

b) first and second means disposed in partially overlying and overlapping relationship upon implantation for tautening the posterior wall of the capsular bag, each of said first and second tautening means being folded back upon itself, said first and second tautening means defining in concert a generally round perimeter encircling said lens;

c) means for suspending said lens from said first and second tautening means adjacent and in contact with the posterior wall; and d) each of said first and second tautening means including connected first and second sections and wherein one of said first section and said second section is more flexible than the other of said first section and said second section and responsive to forces exerted by the capsular bag upon implantation of said intraocular lens, whereby, the more flexible one of said first section and said second section of each of said first and second tautening means will bend radially inwardly into an overlying relationship with the other of said first and second tautening means.

15. The apparatus as set forth in claim 14 wherein said first tautening means comprises a first segment extending from said lens and said first and second sections together extend from said first segment along a general arc of more than 180° and wherein said second tautening means comprises a first segment extending from said lens and said first and second sections together extend from said first segment along a general arc of more than 180°.

16. The apparatus as set forth in claim 15 wherein each of said first segment of said first tautening means and said first segment of said second tautening means is curved toward said lens.

17. The apparatus as set forth in claim 14 wherein said first and second tautening means include means for urging rotation of said lens about its optical axis on imposition of a compressive force upon said intraocular lens.

18. An intraocular lens comprising:

a) an optic for implantation in a human eye;

b) first and second fixation members attached to said optic for supporting said optic from the capsular bag of the eye, each of said fixation members including inner and outer legs;

c) said inner leg of each of said fixation members extending radially outwardly and circumferentially in a first circumferential direction from a respective one of first and second attachment sites on said optic to an intermediate portion of said fixation member, each of said inner legs extending circumferentially for a substantially greater distance than it extends radially;

d) said outer leg of each of said fixation members extending in a second circumferential direction along a respective one of first and second arcs from the intermediate portion of said fixation member to a digital end part of said fixation member, which second circumferential direction is opposite to the first circumferential direction;

e) the first and second arcs being concave toward said optic;

f) each of said outer legs being dimensioned and arranged to be received in the capsular bag and including linearly connected first and second sections, one of said first and second sections being more flexible than the other of said first and second sections to encourage primary bending of the more flexible one of said first and second sections of each of said outer legs in response to forces imposed by the capsular bag; and g) each of said outer legs having a length sufficient to locate the distal end part of each of said fixation members proximate the intermediate portion of the other of said fixation members.

19. An intraocular lens comprising:

a) an optic for implantation in a human eye, said optic including first and second fixation members attached to said optic for supporting said optic in the eye, each of said fixation members including inner and outer legs;

b) said inner leg of each of said fixation members extending radially outwardly and circumferentially in a first circumferential direction from a respective one of first and second attachment sites on said optic to an intermediate portion of said fixation member;

c) said outer leg of each of said fixation members extending in a second circumferential direction along a respective one of first and second arcs from the intermediate portion of said fixation member to a distal end part of said fixation member, which second circumferential direction is opposite to the first circumferential direction, each of said outer legs including a first section and a second section more flexible than said first section to encourage primary bending of said second section of each of said outer legs in response to forces imposed by the capsular bag;

d) the first and second arcs being concave toward said optic; and e) each of said outer legs having a length sufficient to locate the distal end part of each of said fixation members proximate the intermediate portion of the other of said fixation members.

20. An intraocular lens for implantation in a human eye and defining a circular fixation member disposed within the capsular bag on implantation, said intraocular lens comprising in combination:

a) a lens for focusing light entering the eye;

b) first haptic means extending from said lens for fixating said lens within the capsular bag, said first haptic means being folded back upon itself and including first segment means and second segment means folded back upon said first segment means;

c) second haptic means extending from said lens for fixating said lens within the capsular bag, said second haptic means being folded back upon itself and including first segment means and second segment means folded back upon said first segment means of said second haptic means;

d) said second segment means of said first haptic means being laterally displaced from and overlapping with a portion of said second haptic means prior to implantation of said intraocular lens;

e) said second segment means of said second haptic means being laterally displaced from and overlapping with a portion of said first haptic means prior to implantation of said intraocular lens; and f) first means operative upon implantation of said intraocular lens for overlying said second segment means of said first haptic means with a portion of said second haptic means and second means operative upon implantation of said intraocular lens for overlying said second segment means of said second haptic means with a portion of said first haptic means to define the circular fixation member, said first overlying means including a first section of said second segment means being of greater flexibility than the remaining section of said second segment means for bending upon implantation of said intraocular lens in response to forces imposed by the capsular bag upon said first overlying means, said second overlying means including a first section of said second segment means being of greater flexibility than the remaining section of said second segment means for bending upon implantation of said intraocular lens in response to forces imposed by the capsular bag upon said second overlying means.

21. The apparatus as set forth in claim 20 wherein each of said second segment means of said first haptic means and said second segment means of said second haptic means extends through an arc of more than 180°.

* * * * *